US008663600B2

(12) United States Patent
Ulmert

(10) Patent No.: US 8,663,600 B2
(45) Date of Patent: Mar. 4, 2014

(54) DIAGNOSIS OF PROSTATE CANCER

(75) Inventor: David Ulmert, New York, NY (US)

(73) Assignee: Diaprost AB, Helsingborg (SE)

( * ) Notice: Subject to any disclaimer, the term of this patent is extended or adjusted under 35 U.S.C. 154(b) by 376 days.

(21) Appl. No.: 11/059,944

(22) Filed: Feb. 17, 2005

(65) Prior Publication Data
US 2006/0182682 A1 Aug. 17, 2006

(51) Int. Cl.
A61K 49/00 (2006.01)

(52) U.S. Cl.
USPC .......................................................... 424/9.1

(58) Field of Classification Search
None
See application file for complete search history.

(56) References Cited

U.S. PATENT DOCUMENTS

| 4,634,586 A * | 1/1987 | Goodwin et al. ............ 424/1.65 |
| 6,326,471 B1 | 12/2001 | Kokolus et al. |
| 7,053,042 B1 * | 5/2006 | Denmeade et al. ............ 514/1.3 |
| 2004/0203012 A1 * | 10/2004 | Diamandis ........................ 435/6 |

FOREIGN PATENT DOCUMENTS

| WO | 98/21365 A2 | 5/1998 |
| WO | WO 9821365 A2 * | 5/1998 |

OTHER PUBLICATIONS

Kairemo et al., Acta Oncologica, 1993, 32 (7/8):801-805.*
Vaisanen V. et al., "Development of sensitive immunoassays for free and total human glandular kallikrein 2", Clinical Chemistry 2004 United State, vol. 50, No. 9, 2004, pp. 1607-1617, XP002379380, ISSN: 0009-9147.
Chengazi Vaseem U. et al., "Imaging prostate cancer with technetium-99m-7E11-C5.3 (CYT-351)", Journal of Nuclear Medicine, vol. 38, No. 5, 1997, pp. 675-682, XP009065995, ISSN: 0161-5505.
Zhu Lei et al., "Dual-label immunoassay for simultaneous measurement of prostate-specific antigen (PSA)-alpha1-antichymotrypsin complex together with free or total PSA.", Clinical Chemistry, vol. 49, No. 1, Jan. 2003, pp. 97-103, XP002379382, ISSN: 0009-9147.
Becker Charlotte et al., "Sensitive and specific immunodetection of human glandular kallikrein 2 in serum", Clinical Chemistry, vol. 46, No. 2, Feb. 2000, pp. 198-206, XP002379383, ISSN: 0009-9147.
Siivola P. et al., "Time-resolved fluorescence imaging for specific and quantitative immunodetection of human kallikrein 2 and prostate-specific antigen in prostatic tissue sections", Urology 2000 United States, vol. 56, No. 4, 2000, pp. 682-688, XP002379384, ISSN: 0090-4295.
Owen W. J. et al., "Nuclear medicine techniques for the diagnosis and therapy of prostate carcinoma.", European Urology. Sep 2001, vol. 40, No. 3, Sep. 2001, pp. 294-299, XP009065994, ISSN: 0302-2838.
Leinonen J. et al. "Reactivity of 77 antibodies to prostate-specific antigen with isoenzymes and complexes of prostate-specific antigen", Tumor Biology, vol. 20, No. Suppl. 1, Oct. 1999, pp. 28-34, XP000900481, ISSN: 1010-4283.
Stenman U. H. et al., "Summary report of the Td-3 workshop: Characterization of 83 antibodies against prostate-specific antigen", Tumor Biology 1999 Switzerland, vol. 20, No. Suppl. 1, 1999, pp. 1-12, XP001055531, ISSN: 1010-4283.
P. Nurmikko et al., Production and Characterization of Novel Anti-Prostate-specific Antigen (PSA) Monoclonal Antibodies That Do Not Detect Internally Cleaved Lys 145-Lys 146 Inactive PSA, Clinical Chemistry, 46:10, pp. 1610-1618 (2000).

* cited by examiner

Primary Examiner — Hong Sang
(74) Attorney, Agent, or Firm — Brummett TechLaw PLLC

(57) ABSTRACT

Methods for diagnosing prostate cancer, and differentiate prostate cancer from other prostate complications, and use of said method, and diagnosing and monitoring lymph gland metastasis, post operative examinations, and examinations during or after radiation, cytostatic, and androgen treatments are disclosed. The methods comprise injecting tracer-labelled PSA or hK2 specific antibodies, visualising PSA or hK2 producing tissue with the aid of a visualization method, and diagnosing prostate cancer from the difference in visualization.

9 Claims, 4 Drawing Sheets

DIAGNOSIS OF PROSTATE CANCER

FIELD OF THE INVENTION

This invention pertains in general to the field of a diagnostic method, which method diagnoses and distinguishes prostate cancer from other prostate complications, such as benign prostatic hyperplasia, and prostatitis. More particularly the invention relates to the use of said method.

BACKGROUND OF THE INVENTION

Prostate cancer is at the present time the most common form of cancer among men. The prostate is a walnut sized gland in men that produces fluid that is a component in semen. The prostate has two, or more, lobes, or sections, enclosed by an outer layer of tissue. The prostate is located in front of rectum and just below the urine bladder, and surrounds the urethra.

The occurrence of prostate cancer is highest in the northwestern part of Europe and in the United States. The growth of the tumour is usually a procedure that takes place during a long period of time. Prostate cancer is normally a mild form of cancer. In fact, the majority of men diagnosed with prostate cancer do survive, and only a minority of the men encounter a more aggressive form of prostate cancer, which metastasizes in an early stage. This form of prostate cancer may only be curable if it is diagnosed in an early stage, before the cancer has spread to extracapsular tissue.

The most common prostate problem is not prostate cancer, but prostate inflammation Or infection, called prostatitis, and prostate enlargement (benign prostatic hyperplasia or BPH).

It is very common that different prostate problems have similar symptoms, such as frequent and urgent need to urinate, beginning a stream of urine. It is also a fact that a man in the early stages of prostate cancer may have no symptoms at all. This confusing array of symptoms makes a thorough medical examination and testing very important.

Today diagnosis and monitoring of prostate cancer may be performed by measuring the concentration of a prostate specific antigen (PSA) in the blood of the patient. If the concentration of PSA is markedly high in several consecutive measurements, performed at different points of time, the assessment is that there is a probability of prostate cancer. At this point of time a biopsy may be performed to verify prostate cancer.

PSA is a protein, constituted of a single chain of 237 amino acids, that is produced in the secretory cells of the prostate. These secretory cells may be found in the whole prostate gland. PSA is well established and thoroughly researched marker in respect of prostate cancer. By comparison with healthy cells the production of PSA is lower in malign cells and higher in hyperplastic cells. It is therefore contradicting that in fact the concentration of PSA is higher in blood from men suffering from prostate cancer. However, one explanation may be that the malign cells have a deteriorated cell structure, and are therefore more permeable to PSA.

Men suffering from benign prostatic hyperplasia (BPH) do also have an increased concentration of PSA in the blood. The increased concentration of PSA, in the blood of men with BPH, is directly proportional to the volume increase of the prostate gland. Also men suffering from prostatitis and gland trauma have an increased concentration of PSA in the blood.

This presents a problem in the diagnosis and monitoring of the different prostate complications. It may be impossible to distinguish between the different complications without performing biopsies of the prostate gland. A biopsy is a surgical procedure, which cause pain and discomfort. Patients awaiting a biopsy may suffer from anxiety prior to the surgical procedure, and it is common that the patient therefore has to take some kind of anxiolytic before the surgical procedure. Other problems with biopsy are that the tumour is missed, which may result in an erroneous diagnosis; risk of infection; the concentration of PSA increases after biopsy, since the cell structure is damaged and the permeation of PSA therefore increases; and formation of scars, which results in an altered structure of the prostate tissue that render future biopsy procedures difficult. Further problems with biopsy are transient haematuria (blood in the urine) and the use of blood-thinning agents.

Another important serine protease, which may be suitable for future diagnosis of prostate malfunction, is human glandular kallikrein 2 (hK2). The gene coding hK2 is located on chromosome 19, together with the gene coding for PSA. hK2 is expressed mainly in the prostate tissue, just as PSA. Immunohistochemical research in respect of hK2 has shown that hK2 is expressed in relation to the level of differentiation. This means that hK2 is expressed in a higher yield in tissue of low differentiation, such as tissue subjected to prostate cancer, and in a lower yield in tissue of high differentiation, such as tissue subjected to BPH.

Positron Emission Tomography (PET) is today used as a radio diagnostic method to detect and evaluate neoplasia. PET utilises the increased level of glycosylation in malign tissue. Radiolabelled glucose analogues are injected intravenously. Thereafter, the gamma radiation is detected to determine the consumption of glucose. Areas comprising cells with a high consumption of glucose are visualised as areas of high attenuation. A three dimensional picture may be created by adding picture screens, which have been produced by the tomography. This technique may be combined with computer tomography (CT) or magnetic resonance tomography (MRT), to obtain the exact anatomic location of the attenuated structure.

Thus, there is a need for a new diagnostic method for establishing and distinguishing prostate cancer from other prostate complications, such as prostatitis, and benign prostatic hyperplasia.

Hence, an improved diagnostic method for establishing and distinguishing prostate cancer would be advantageous and in particular a diagnostic method allowing for differentiation between prostate cancer and other prostate complications, such as benign prostatic hyperplasia, and prostatitis, which diagnostic method also may be used to investigate metastasis, such as lymph gland metastasis, post operative examinations, and examinations during or after radiation, cytostatic, and androgen treatments, would be advantageous, said method also avoiding the above deficiencies in respect of biopsy.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a diagnostic method according to the appended patent claims.

According to one aspect of the invention, a diagnostic method is provided, which method diagnoses and distinguish prostate cancer from other prostate complications, such as benign prostatic hyperplasia, and prostatitis, which method includes visualisation of PSA and/or hK2 producing tissue with tracer-labelled PSA and hK2 specific antibodies.

According to another aspect of the invention, a diagnostic method is provided, which method may be used to investigate metastasis, such as lymph gland metastasis.

According to yet another aspect of the invention, a diagnostic method is provided, which method may be used to perform examinations during or after radiation, cytostatic, and androgen treatments.

According to another aspect of the invention, tracer-labelled antibodies, that are specific for PSA and/or hK2, are provided, which labelled antibodies are used to visualize PSA and/or hK2 producing tissue.

According to another aspect of the invention, use of said methods are provided.

The diagnostic method according to the present invention has the advantage over the prior art that it allows for diagnosis of prostate cancer, and distinction between prostate cancer and other prostate complications, such as benign prostatic hyperplasia, and prostatitis, while simultaneously erasing the deficiencies mentioned above in respect of biopsy, and said diagnostic method may also be used to investigate metastasis, such as lymph gland metastasis, post operative examinations, and examinations during or after radiation, cytostatic, and androgen treatments.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on embodiments of the present invention applicable to a diagnostic method of prostatic cancer. However, it will be appreciated that the invention is not limited to this application but may be applied to many other medical examinations, and diagnostic investigations, including for example lymph gland metastasis, post operative examinations, and examinations during or after radiation, cytostatic, and androgen treatments. In respect of diagnostic investigation of metastasis the metastases will be visible in lymph glands and lymph vessels, since PSA and hK2 pass these regions.

In an embodiment of the invention, antibodies that are specific for PSA and are labelled with a tracer are then injected into the body, such as intravenously. Then the tracer labelled antibodies, that are specific for PSA, bind to tissues that produce corresponding antigens, in this case PSA. The biologic structures, to which the tracer labelled PSA specific antibodies are bound, are subsequently visualised with a suitable radiologic visualisation method, such as PET-scan or other scintigraphic methods by means of the tracer.

Thereafter, antibodies, that are specific for hK2, are labelled with a tracer. These antibodies are then injected intravenously. The tracer labelled antibodies, that are specific for hK2, bind to tissues that produce corresponding antigens. The biologic structures, to which the tracer-labelled hK2 specific antibodies are bound, are subsequently visualised with a suitable radiologic visualisation method, such as PET-scan or other scintigraphic methods.

In yet another embodiment the order may be reversed, i.e. the visualization hK2 producing tissue is performed before the visualisation of PSA producing tissue.

In another embodiment of the present invention the tracer-labelled antibodies are injected in any other way into the bloodstream, or the lymphatic system, such as intra-arterial infusion etc.

Variations in respect of attenuation are directly corresponding to production and concentration relations of PSA and hK2. These variations are then used to obtain diagnostic information.

The visualizations of PSA and hK2 antibody bindings, obtained from the radiologic visualisation methods mentioned above, are then combined. From the attenuations it is possible to directly determine whether the investigated tissue is PSA producing, hK2 producing, or both. In respect of this determination it will be possible to distinguish prostate cancer from other prostate disorders, such as benign prostatic hyperplasia, and prostatitis.

Figure 1:
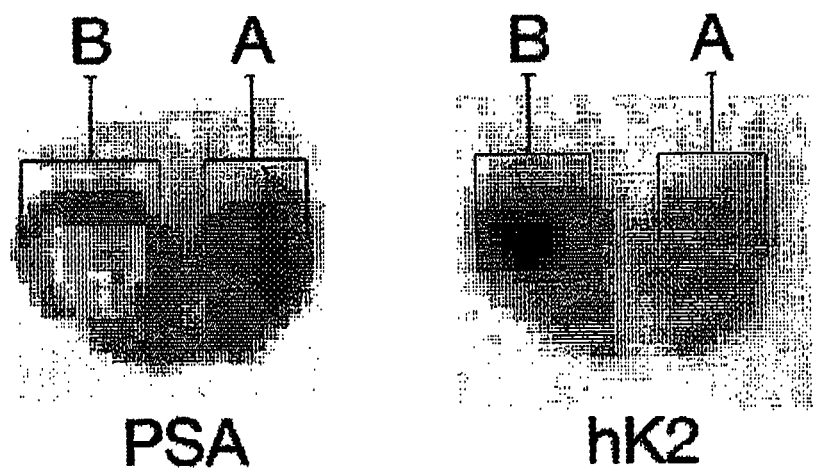
FIG. 1 is a schematic illustration of the combination of visualisation with both PSA producing tissue and hK2 producing tissue in a cancerous prostate.

In one example the visualisation of PSA producing tissue reveals that a part A of a prostate, according to FIG. 1, has a higher PSA production than a part B. When this visualisation is combined with the visualisation of hK2 producing tissue, where the part A has a lower hK2 production than the part B, the physician will be able to establish prostate cancer in the part B.

Figure 2:
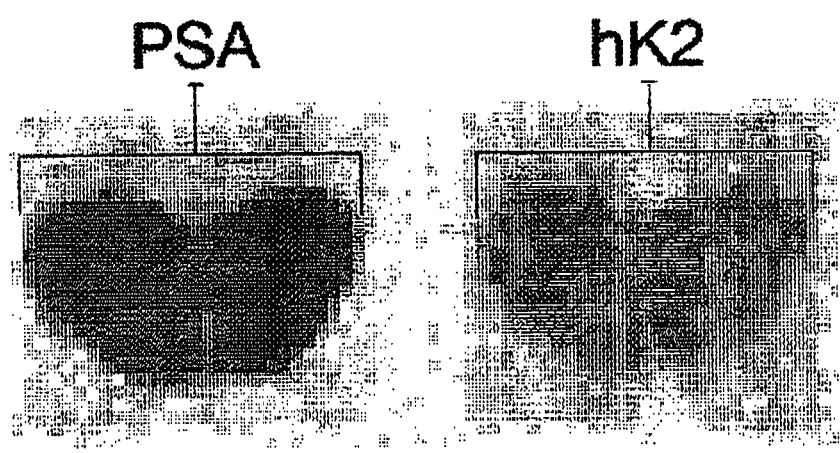
FIG. 2 is a schematic illustration of the combination of visualisation with both PSA producing tissue and hK2 producing tissue in a non-cancerous prostate.

In another example, according to FIG. 2, the visualisation of PSA producing tissue reveals that a prostate has an even, and relatively high, production of PSA. When this visualisation is combined with the visualisation of hK2 producing tissue, where the production of hK2 is evenly low in the prostate, the physician will be able to establish that there is no prostate cancer.

In another embodiment of the invention the visualisation of PSA producing tissue or the visualisation of hK2 producing tissue may be used separately to visualise the difference in PSA and hK2 production, respectively, in the prostate. This embodiment presents the advantage of being time saving in respect of performing two intravenous injections of antibodies, and subsequently two visualisations of the prostate. Nevertheless, the combination of the visualisation of PSA producing tissue and the visualisation of hK2 producing tissue presents a more reliable diagnose and distinction in respect of prostate cancer, and other prostate disorders, such as benign prostatic hyperplasia, and prostatitis, since two indications of possible disorders in respect of antigen production are obtained.

Figure 3:
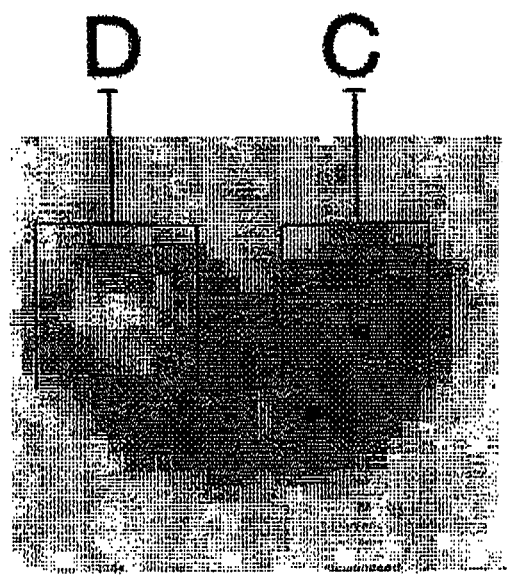
FIG. 3 is a schematic illustration of only visualisation with PSA producing tissue in a cancerous prostate.

In an example of visualisation with only the aid of the tracer labelled antibodies, that are specific for PSA, according to FIG. 3, a part C of a prostate has a higher PSA production than a part D. The physician will be able to establish prostate cancer in the part D, since part D differentiate in respect of PSA production from part C.

Figure 4:
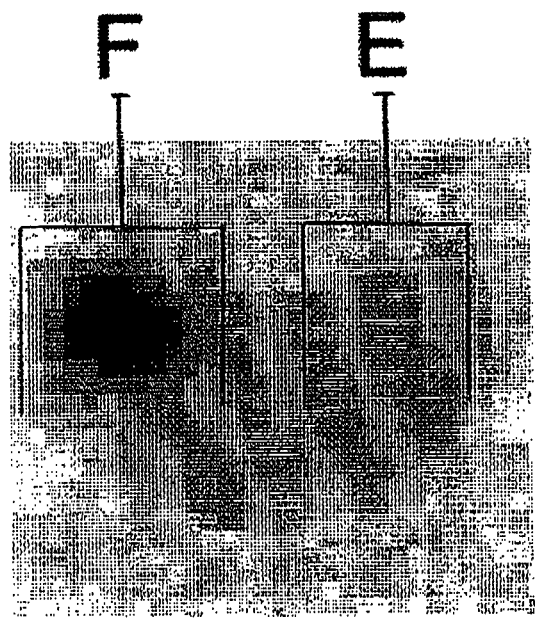
FIG. 4 is a schematic illustration of only visualisation with PSA producing tissue in a cancerous prostate.

In yet an example of visualisation with only the aid of the tracer labelled antibodies, that are specific for hK2, according to FIG. 4, a part E of a prostate has a lower hK2 production than a part F. The physician will be able to establish prostate cancer in the part F, since part F differentiate in respect of PSA production from part E.

The visualisation methods in the embodiments according to the present invention reflect the production of PSA and hK2. These methods aim at visualise malign and non-malign patho-biological conditions, anatomic characteristics, size of tumour, and degree of malignancy. According to the above it will be possible to perform examinations in respect of metastasis, and lymph glands.

In still another embodiment of the present invention the visualisations obtained according to above may be combined with other radiological visualisation methods, such as computed tomography (CT), computerized axial tomography (CAT), and magnetic resonance tomography (MRT).

The term PSA is intended to include every known form of PSA, such as free PSA, precursor forms of PSA, internally nicked forms of PSA, low molecular weight free PSA, standard weight free PSA, inactive mature PSA, truncated forms of PSA, glycosylation variants of PSA, BPSA, inactive pro-PSA, and every complex of PSA, such as PSA bound to α1-antichymotrypsin (ACT), α1-protease inhibitor (API), and α2-macroglobulin (AMG).

PSA, secreted from cancer cells, is in a more active state in comparison with PSA, secreted from BPH tissue. In the extracellular fluid PSA may be subjected to proteolytic degradation, thus leading to loss of activity and formation of complexes.

Thus, it is also within the scope of the present invention to label compounds or entities, such as ACT, API, and AMG, bound or complexed to/with PSA.

The term hK2 is intended to include all isomeric forms of hK2, and any molecule or protein in complex with hK2.

Most of the hK2 found in seminal plasma is inactive and complexed with protein C inhibitor (PCI). It is also possible that hK2 forms complexes with other extracellular protease inhibitors. In vitro studies show that hK2 may bind to $\alpha_2$-antiplasmin ($\alpha_2$-AP), ACT, AMG, anti-thrombin III (ATIII), C1-inactivator and plasminogen activator inhibitor-1 (PAI-1).

Thus, it is also within the scope of the present invention to label compounds, molecules, proteins or any other entity, such as PCI, $\alpha_2$-antiplasmin ($\alpha_2$-AP), ACT, AMG, anti-thrombin III (ATIII), C1-inactivator and plasminogen activator inhibitor-1 (PAI-1), bound or complexed to/with hK2.

The term "tracer label" is intended to include all possible radio-isotopes or the like, which may bind to PSA or hK2 antibodies, and which may be used for detection with a positron camera, such as gamma positron camera, or other radiological visualisation technique. An example of a tracer label is technetium-99m, but it is of course within the scope of the present invention to use other suitable tracer labels, which tracer labels fulfil the requirements for labelling PSA and hK2 specific antibodies.

The term "antibody" is intended to include both human and non-human antibodies, such as 4D4, 5C3, 241, 2E9, H117, and 5A10 in respect of PSA, and 11B6, and 7G1 in respect of hK2. It is of course within the scope of the present invention to use other suitable antibodies, which antibodies fulfil the requirements of PSA and hK2 specific antibodies.

In yet another embodiment of the invention the injection of tracer-labelled antibodies is performed in the vicinity of the tissue or organ to be visualised. This embodiment has the advantage of somewhat concentrating the tracer-labelled antibodies on the area to be visualised. More tracer-labelled antibodies may reach the area of interest.

The invention can be implemented in any suitable form. However, preferably, the invention is implemented as diagnostic method in respect of prostate cancer, and distinction of prostate cancer from other prostate complications, such as benign prostatic hyperplasia, and prostatitis. The clinical field of use in respect of the produced visualisations are for example detection and monitoring of prostate cancer and other prostate complications, such as benign prostatic hyperplasia, and prostatitis, and examinations in respect of metastasis and treatments. The present invention is also intended for other urological clinic application, such as post operative evaluation of radical treatment and treatment examinations during or after lymph gland metastasis, radiation, cytostatic, and androgen treatments. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An in vivo method for diagnosing prostate cancer, said method consisting essentially of the steps of:
   injecting tracer-labeled antibodies specific for hK2 into a subject suspected to have prostate cancer,
   diagnosing prostate cancer by visualising biological structures to which the tracer-labeled hK2 specific antibodies are bound.

2. A method according to claim 1, wherein said visualising is a radiologic PET-scan visualisation.

3. A method according to claim 1, wherein said tracer-label is technetium-99m.

4. A method according to claim 1, wherein said biological structures are visualised using radiologic PET-scan visualisation coupled with a second radiological visualisation method selected from the group consisting of computed tomography (CT) visualisation, computerized axial tomography (CAT) visualisation and magnetic resonance tomography (MRT) visualisation.

5. The method according to claim 1, wherein the method is for investigating metastasis.

6. The method according to claim 5, wherein the method is for examining or monitoring lymph gland metastasis.

7. A method for examination, or monitoring, of lymph gland metastasis, post-operative examinations, and examinations during or after radiation, cytostatic, and androgen treatments of a subject previously diagnosed as having prostate cancer, said method consisting essentially of the steps of:
   injecting tracer-labeled antibodies specific for hK2 into a subject previously diagnosed as having prostate cancer,
   visualising hK2 by PET-scan.

8. A method for differentiating prostate cancer from other prostate conditions, said method consisting essentially of the steps of:

injecting tracer-labeled antibodies specific for hK2 into a subject suspected to have prostate cancer, differentiating prostate cancer from other prostate conditions by visualising biological structures to which the tracer-labeled hK2 specific antibodies are bound.

9. The method for differentiating prostate cancer from other prostate conditions according to claim 8, wherein injecting tracer-labeled antibodies specific for hK2 into a subject comprises:

an intravenous injection of the tracer-labeled antibodies specific for hK2 into the subject.

* * * * *

UNITED STATES PATENT AND TRADEMARK OFFICE
CERTIFICATE OF CORRECTION

| | | |
|---|---|---|
| PATENT NO. | : 8,663,600 B2 | Page 1 of 1 |
| APPLICATION NO. | : 11/059944 | |
| DATED | : March 4, 2014 | |
| INVENTOR(S) | : Ulmert | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 521 days.

Signed and Sealed this
Eighth Day of September, 2015

Michelle K. Lee
*Director of the United States Patent and Trademark Office*